United States Patent
Gambale et al.

(10) Patent No.: US 6,629,987 B1
(45) Date of Patent: Oct. 7, 2003

(54) CATHETER POSITIONING SYSTEMS

(75) Inventors: Richard A. Gambale, Tyngsboro, MA (US); Stephen J. Forcucci, Medford, MA (US); Chirag B. Shah, Nashua, NH (US); Michael F. Weiser, Groton, MA (US); Sean Forde, Watertown, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/364,520

(22) Filed: Jul. 30, 1999

(51) Int. Cl.[7] .......................... A61M 29/00; A61M 5/32
(52) U.S. Cl. ...................... 606/198; 606/191; 604/106; 604/107; 604/108; 604/109; 604/175
(58) Field of Search ................................. 604/104–109, 604/14, 17, 27, 174, 175, 264, 523; 606/191, 194, 198

(56) References Cited

U.S. PATENT DOCUMENTS

| | | | |
|---|---|---|---|
| 3,680,544 A | | 8/1972 | Shinnick et al. |
| 4,030,505 A | * | 6/1977 | Tessler |
| 4,894,057 A | | 1/1990 | Howes |
| 5,112,310 A | * | 5/1992 | Grobe ................... 604/103.03 |
| 5,180,366 A | | 1/1993 | Woods |

(List continued on next page.)

FOREIGN PATENT DOCUMENTS

| | | |
|---|---|---|
| DE | 19703482 | 1/1997 |
| EP | 0 490 459 A1 | 6/1992 |
| EP | 0 717 969 A2 | 6/1996 |
| EP | 0 830 873 A2 | 3/1998 |
| EP | 0 853 921 A2 | 7/1998 |
| EP | 0 953 320 A2 | 11/1999 |
| WO | WO 90/06723 | 6/1990 |
| WO | WO 94/27612 | 12/1994 |
| WO | WO 95/133511 | 12/1995 |
| WO | WO 96/20698 | 7/1996 |
| WO | WO 97/42910 | 7/1997 |
| WO | WO 97/38730 | 10/1997 |
| WO | WO 97/45105 | 12/1997 |
| WO | WO 98/23228 | 6/1998 |
| WO | WO 98/29148 | 7/1998 |
| WO | WO 98/46115 | 10/1998 |
| WO | WO 99/21510 | 5/1999 |
| WO | WO 99/53863 | 10/1999 |

*Primary Examiner*—Brian L. Casler
*Assistant Examiner*—Catherine Serke
(74) *Attorney, Agent, or Firm*—Kirkpatrick & Lockhart LLP

(57) ABSTRACT

The present invention provides a catheter positioning system which serves to control and stabilize a distal end of a catheter at a treatment site within a patient so that a medical procedure can be performed with accuracy. Generally, the positioning system operates by providing a deformable mechanical members at the distal end of the catheter which can be operated from the proximal end of the catheter to extend radially outward to engage surrounding tissue adjacent to treatment site. In one embodiment of the invention a flexible superstructure comprising the plurality of flexible veins extending longitudinally along the distal end of the catheter can be deformed to bow radially outward to engage surrounding tissue. The distal tip of the catheter joined to one of the veins was correspondingly displaced or rotated angularly as the veins bow outward. In another embodiment radially projecting fingers are joined to the distal end of the catheter, which remain retracted during navigation of the catheter to the treatment site then are extended outward to penetrate the tissue and secure the catheter at the treatment site upon being actuated from the proximal end of the catheter by a physician. Methods of positioning a catheter are also disclosed. The inventive device and method are particularly useful in catheter based procedures carried out in large body lumens or in cavities of body organs. In particular, the invention may be useful in delivering implants percutaneously through the left ventricle into the myocardium of the heart.

17 Claims, 8 Drawing Sheets

U.S. PATENT DOCUMENTS

| | | | |
|---|---|---|---|
| 5,267,960 A | * 12/1993 | Hayman et al. | |
| 5,275,610 A | * 1/1994 | Eberbach | 606/198 |
| 5,429,144 A | 7/1995 | Wilk | |
| 5,464,395 A | * 11/1995 | Faxon et al. | 604/103.02 |
| 5,562,922 A | 10/1996 | Lambert | |
| 5,655,548 A | 8/1997 | Nelson et al. | |
| 5,690,643 A | 11/1997 | Wijay | |
| 5,733,325 A | * 3/1998 | Robinson et al. | 623/1 |
| 5,755,682 A | 5/1998 | Knudson et al. | |
| 5,810,836 A | 9/1998 | Hussein et al. | |
| 5,855,563 A | 1/1999 | Kaplan et al. | |
| 5,954,745 A | * 9/1999 | Gertler et al. | 606/159 |
| 5,971,993 A | 10/1999 | Hussein et al. | |
| 5,980,548 A | 11/1999 | Evans et al. | |
| 6,027,518 A | * 2/2000 | Gaber | 654/105 |
| 6,045,565 A | 4/2000 | Ellis et al. | |
| 6,200,280 B1 | * 3/2001 | Brenneman et al. | 601/41 |
| 6,217,554 B1 | * 4/2001 | Green | 604/164.01 |
| 6,302,870 B1 | * 10/2001 | Jacobsen et al. | 604/164.09 |
| 6,306,163 B1 | * 10/2001 | Fitz | 606/198 |

* cited by examiner

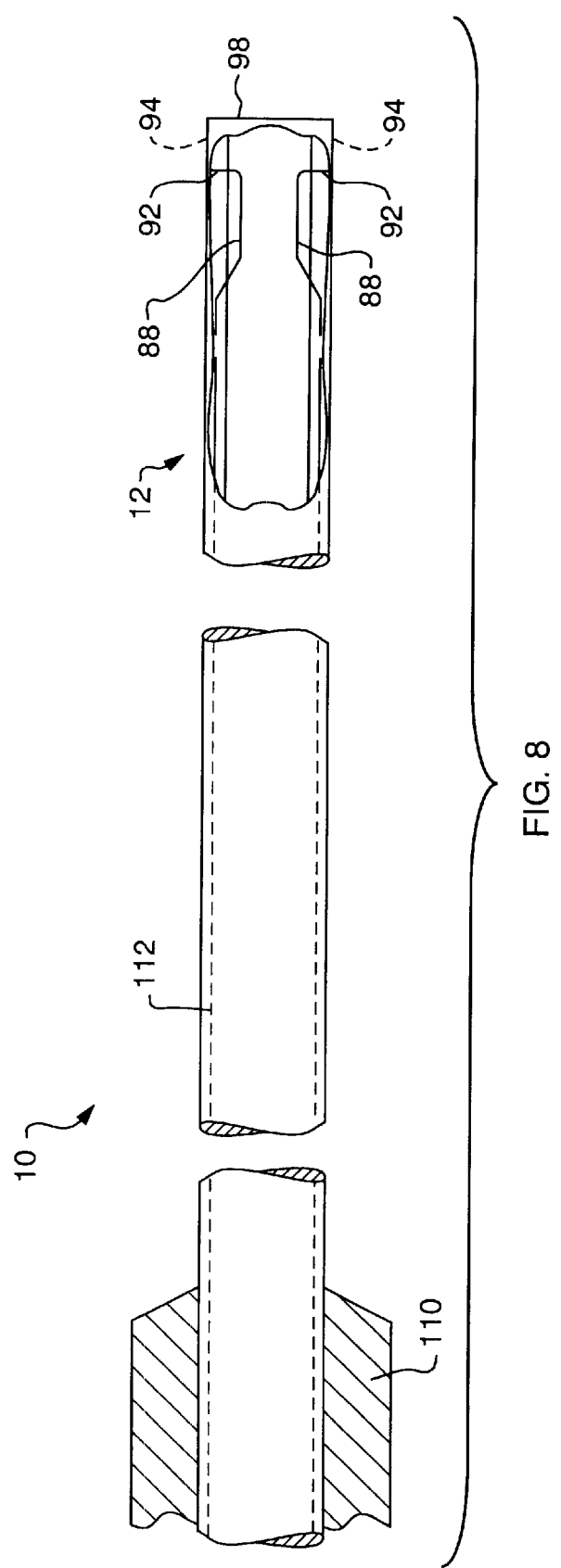

CATHETER POSITIONING SYSTEMS

FIELD OF THE INVENTION

This invention relates to devices and methods for accurately and securely positioning the distal end of a catheter during a medical procedure. Specifically, devices and methods are provided for controlling the movement of the distal end of the catheter procedure while being used in a body lumen or organ cavity.

BACKGROUND OF THE INVENTION

In many procedures utilizing catheters, one of the most difficult challenges is effectively navigating the catheter to its intended location and maintaining the distal end, or operating end of the catheter at the intended locations throughout the medical procedure. In cases where the catheter is placed through a narrow body lumen such as a blood vessel, maintaining the orientation of the distal end of the catheter within the lumen may be somewhat manageable. However, in applications where the body lumen is relatively large in comparison to the diameter of the catheter, or the catheter is delivered to a cavity of a body organ such as the left ventricle of the heart, the distal end of the catheter will likely have a greater range of movement and, thus, may be more difficult to position accurately.

Several procedures utilizing catheters percutaneously delivered to the ventricle of the heart have been disclosed. For example, various methods of treating ischemic myocardial tissue involve introducing a catheter into the ventricle of the heart. Creating channels in the heart tissue with a laser catheter is disclosed in U.S. Pat. No. 5,769,843 (Abella et al.) and U.S. Pat. Nos. 5,380,316 and 5,389,096 (Aita). The patents disclose utilizing laser energy discharged from the distal end of a catheter to ablate tissue from the heart wall to create a channel. U.S. Pat. No. 5,429,144 (Wilk) and International patent application publication no. WO 9849964 disclose delivering an implantable stent device into the heart wall from a catheter that has been percutaneously introduced into the ventricle of the heart. Stabilizing the distal end of such catheters during the given treatment procedure would appear to be critical.

It would be advantageous to provide a systemication of a compressive force delivered through a pull wire that extends through the catheter. The expansion of the flexible vanes increases the profile of the catheter at its distal end such that the vanes will contact interior wall surfaces of the body lumen or organ in which the catheter is placed thereby preventing unwanted movement of the catheter.

SUMMARY OF THE INVENTION

The present invention provides various mechanisms for positioning the distal end of a catheter at its intended treatment site within a patient. Two approaches to positioning the distal end of the catheter are disclosed. In a first embodiment, the distal end of the catheter employs a collapsible superstructure which causes the distal tip of the catheter mounted thereto to change direction so that the distal opening of the catheter can be directed to the intended tissue site. The superstructure is comprised of two flexible veins mounted along the side wall of the distal end of the catheter parallel to the longitudinal axis of the catheter that are biased to bow radially outward upon an application of a compressive force delivered through a pull wire that extends through the catheter. The expansion of the flexible veins increases the profile of the catheter at its distal end such that the veins will contact interior wall surfaces of the body lumen or organ in which the catheter is placed thereby preventing unwanted lateral movement of the catheter. The distal tip of the catheter is mounted to the distal end of one of the vanes so that the vane lies along the longitudinal axis of the catheter when the vanes are unstressed. Therefore, when the vanes are bowed radially outward the angular displacement of the vane at the connection point with the distal tip of the catheter, away from the longitudinal axis of the catheter, causes the distal tip to have a corresponding angular displacement. The variable angular displacement of the tip during displacement of the vanes provides a steering mechanism for the tip of the catheter so that it may be navigated to a particular tissue location.

In another aspect of the invention, the catheter positioning system comprises radially extending fingers at the distal end of the catheter which extend outward into surrounding tissue at the intended location to secure the catheter. The radially extending fingers remain retracted within the catheter during navigation to the intended treatment site and are extended to engage tissue upon reaching the treatment site. The number of radially extending fingers may vary depending on the retention force of the catheter necessary to perform the intended procedure. At least one of the fingers may be tubular, such as a hypotube. The tubular finger may be used to deliver a therapeutic agent to the tissue engaged by the finger. Additionally, the stiffness of the catheter shaft may be varied to help provide the desired directional stability of the catheter when restrained by the positioning system.

Various mechanisms for actuating the radially extending fingers may be employed. The fingers may be resiliently biased radially inward in the recessed position and forced into the extended position by another device advanced through the central lumen of the catheter. Alternatively, the fingers may be actuated by control cables extending along the length of the catheter either through a central lumen or through smaller independent lumens in the side wall of the catheter. The proximal ends of such cables can be joined to a handle mechanism joined to the proximal end of the catheter to facilitate actuation by a physician.

It is an object of the present invention to provide a system for effectively controlling the position of the distal end of a catheter that has been navigated to a treatment site in a patient.

It is another object of the invention to provide a catheter positioning system that operates to locate the distal end of the catheter and control the orientation of its distal tip by deforming an external superstructure joined to the distal end of the catheter.

It is another object of the invention to provide a catheter positioning system that operates to locate the distal end of a catheter by providing radially extending fingers that penetrate into adjacent tissue.

It is another object of the invention to provide a method for positioning the distal end of a catheter that comprises actuating a mechanical component at the distal end of the catheter to engage surrounding tissue.

It is another object of the invention to provide a catheter positioning system that is easy to use and economical to incorporate into a catheter design.

BRIEF DESCRIPTION OF THE DRAWINGS

The foregoing and other objects and advantages of the invention will be appreciated more fully from the following further description thereof, with reference to the accompanying diagramatic drawings wherein:

FIG. 8 is a diagrammatic side view of a catheter equipped with an embodiment of the catheter positioning system and control handle.

DESCRIPTION OF THE ILLUSTRATIVE EMBODIMENTS

Figure 1:
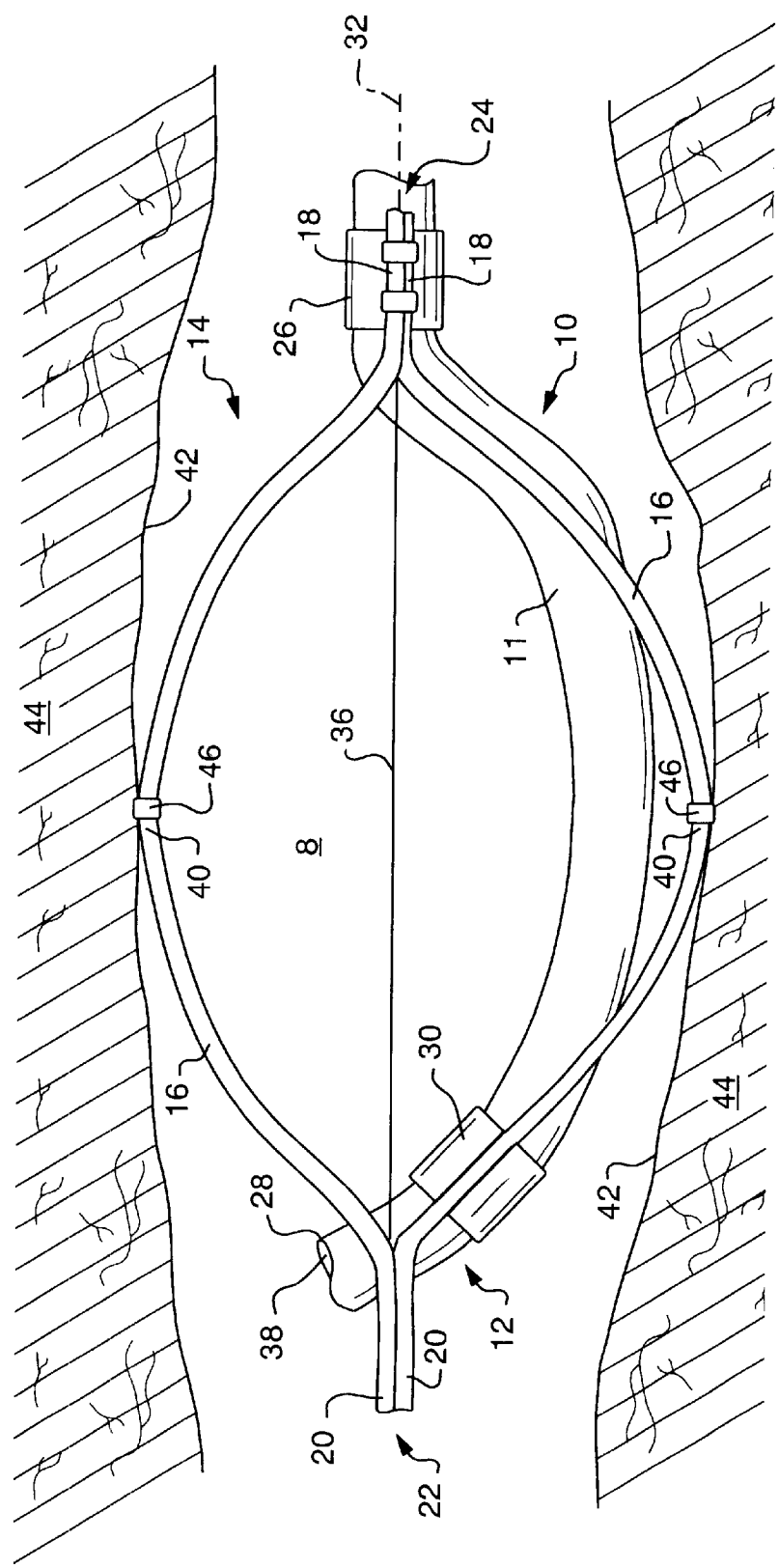
FIG. 1 is a side view of an embodiment of the catheter positioning system extended in a body lumen.

FIG. 1 shows a side view of a distal end 12 of a catheter 10 equipped with an embodiment of the catheter positioning system. The catheter comprises an elongate shaft 11 of conventional construction, extruded from polymeric material and having at least one lumen. A superstructure positioning system 14 at the distal end of the catheter is comprised of several elongate resilient vanes 16 each having proximal and distal ends 18 and 20, respectively. The distal ends 20 of each vane are joined at a distal joint 22 by such a means as soldering or welding at a point that is proximal to the distal tip 28 of the catheter. Distal connector band 30 located adjacent the distal tip 28 of the catheter joins a portion of a single vane fixedly to the catheter shaft 11 at a point along the vane that is slightly proximal from the distal connection 22. Connector bands 26 and 30 may be formed of a polymer or any suitable material capable of joining both the catheter shaft 11 and a vane 16. The bands may even comprise only adhesive without a specific band structure. The purpose of the bands is to form a joint, preferably fixed, between the vane and the catheter shaft at their given location and to maintain the captured portion of the vane parallel with the longitudinal axis 32 of the catheter 10. The proximal ends 18 of the vanes are joined at a proximal joint 24 at proximal connector band 26 which fixes the joint 24 and thus the proximal ends 18 of the vanes to the catheter shaft 11.

Figure 2A:
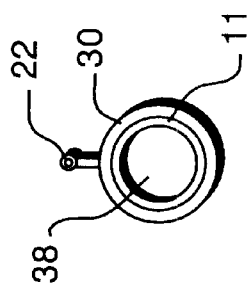
FIG. 2A is an end view of an embodiment of the catheter positioning system.
Figure 2B:
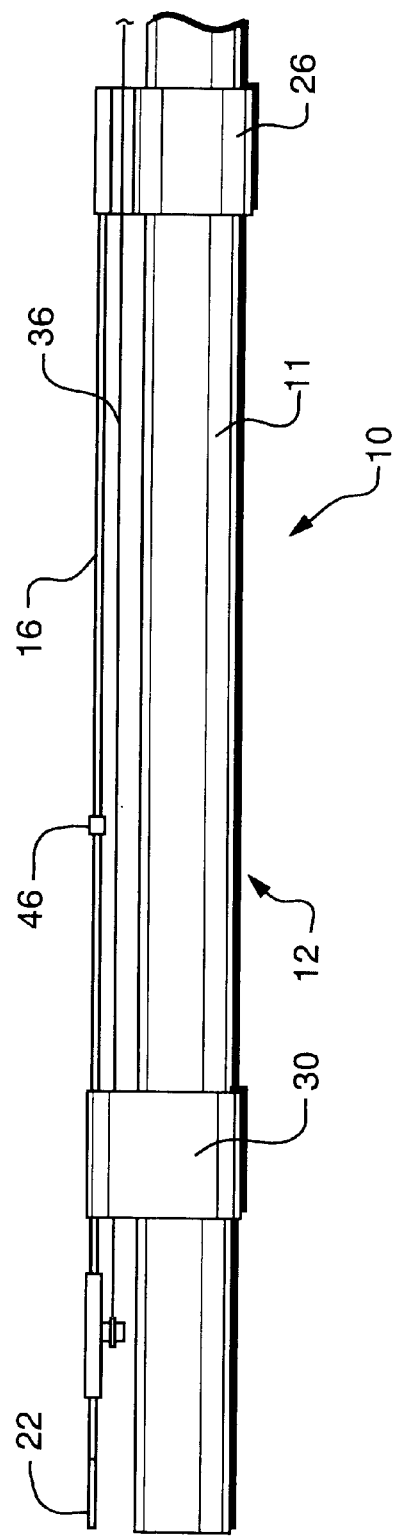
FIG. 2B is a side view of an embodiment of the catheter positioning system retracted and rotated 90° from the FIG. 1 diagram.

FIG. 2A shows an end view of the catheter 10 and FIG. 2B shows a side view 15 of the catheter and positioning system retracted and rotated 90° from the view shown in FIG. 1. A control mechanism comprises a pull wire 36 that is joined to the distal connection 22 at one end and extends proximally to the proximal end (not shown) of the catheter. The control mechanism or pull wire extends along the exterior of the catheter shaft 11 through the range encompassed by the length of the vanes 16. However, from proximal connection 24 and band 26, the control mechanism or pull wire 36 may pass through the side wall of a catheter and extend through the lumen 38, or may continue proximally along the exterior of the catheter.

Placing the pull wire in tension applies a compressive force on the vanes 16 causing it to buckle radially outward so that vane midpoints 40 engage the surface 42 of surrounding tissue 44 to locate the catheter as is shown in FIG. 1. Sensing bands 46 may be placed at the midpoints 40 of vanes 16 for the purpose of contacting and sensing properties of the tissue near the treatment area to which the catheter is delivered. Sensing bands 46 may be configured to perform a variety of useful functions such as mapping the surface of the tissue, detecting electrical or thermal data of the tissue, or for other purposes.

The vanes 16 may be formed from a filament of any material providing resilient behavior and body temperature. The vanes may be formed from a metal such as stainless steel or nitinol or may be formed from a polymer material. The vanes can be any cross-sectional shape such as a round wire or a rectangular ribbon, but preferably should having a shape and configuration that encourages the vanes to bow radially outward in opposite directions when they buckle under compressive loading. The pull wire 36 may be made from any material having sufficient strength to place tension on the vanes. Materials such as metallic wire or a polymer would be suitable. The control mechanism or pull wire may be joined to the distal connection 22 by any suitable means such as soldering, welding or adhesive.

When there is no force on control mechanism or pull wire 36, vane 16 and distal end 12 of catheter shaft 11 are in a retracted, straight position due to the natural resiliency of the catheter shaft 11 and the vanes. Upon application of tension to control mechanism or pull wire 36, the distal connection 22 is pulled proximally relative to the catheter causing vanes 16 and distal end of catheter shaft 12 to buckle and bow radially outward. Vanes 16 eventually come into contact with tissue surfaces 42 as their profile increases within body cavity 8. With vane midpoints 40 wedged against tissue surfaces 42, the distal end 12 of the catheter is stabilized because its side-to-side movement is prevented. In this condition, the procedures may be performed through the catheter and the intended treatment site may reliably be reached by instruments passed through the catheter lumen 38. When tension is released on the control mechanism or pull wire 36, the vanes and catheter resiliently return to their straight configuration and the catheter may be removed from the treatment location.

Another control feature of the superstructure positioning system is the angular displacement of the distal tip 28 of the catheter 10 corresponding to the extension of vanes 16. Due to the parallel arrangement of the vane 16 and distal end of the catheter 12 at distal connector band 30, a longitudinal axis of the catheter 32 at the distal tip 28 rotates an amount of angular displacement corresponding to the magnitude angular displacement of the vane away from its original unstressed position. As greater tension is applied to the pull wire 36 to cause further buckling of the vane 16, angular displacement of the distal tip 28 of the catheter will continue to increase. Therefore, the angular displacement can be variably controlled by the operators manipulation of the control mechanism or pull wire. This angular displacement control provides a steering mechanism to pinpoint treatment sites on the tissue surface 42 of the body conduit or cavity. Although two vanes are shown in the drawings discussed herein in the present embodiment, more resilient vanes can be used to construct a catheter positioning device in accordance with the present invention.

Figure 3A:
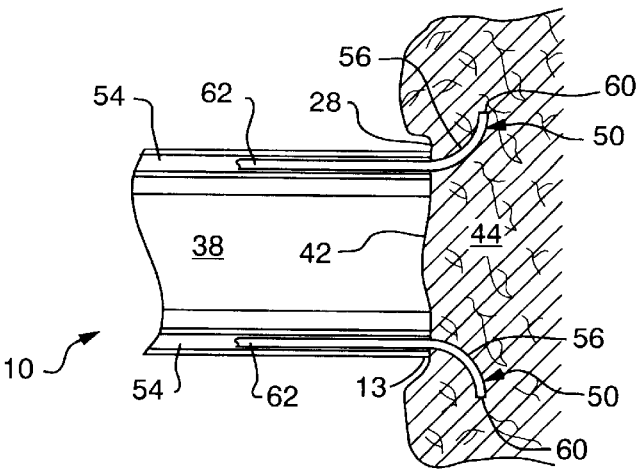
FIG. 3A is a side cut-away view of an embodiment of the catheter positioning system having radially extending fingers contained in individual catheter lumens and extending from the distal end of the catheter.

FIG. 3A shows a cut-away side view of another embodiment of the catheter positioning system that utilizes radially projecting fingers 50 to engage and penetrate tissue 44. Embodiments of the catheter positioning system employing radially projecting fingers can have various configurations; however, generally, the fingers should be formed from a resilient filament material of any cross-sectional shape and of metallic or polymeric material. The resiliently projecting fingers penetrate or extend to penetrate tissue that has come to surround their extension path due to distal pressure applied on the catheter 10 causing tissue 44 to herniate around the distal tip 28 and side surface 13 of the catheter.

At least one of the projecting fingers may be a tubular member capable of delivering a therapeutic agent to the tissue engaged by the distal end of the finger. A stainless steel hypodermic tube may be use. The proximal end of the tubular finger should be joined to a pressurizable source of a therapeutic agent. Once the distal end of the finger is extended radially outward into contact with the tissue the agent may be delivered under pressure to the tissue site. Various therapeutic agents may be used depending on the treatment involved. In delivering angiogenic implants to the myocardium agents such as growth factors cellular compositions or gene therapies may be delivered in liquid or gel form.

Figure 3B:
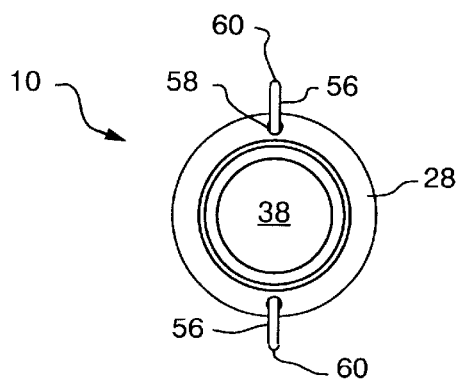
FIG. 3B is an end view of the embodiment shown in FIG. 3A.

FIG. 3B shows an embodiment wherein the projecting fingers 50 are slidably received within auxiliary lumens 54, which are much smaller than and run parallel to main lumen 38. For frame of reference, auxiliary lumens may measure on the order of 0.012 inch inside diameter while main lumen 38 may measure on the order of 0.068 inch inside diameter. The outside diameter of catheters discussed in connection with this invention may be on the order of 0.105 inch. Distal ends 56 of projecting fingers are precurved and arranged within the lumens to project radially outward away from the catheter when not confined by the lumens 54 and reach their unstressed condition. During advancement of the catheter 10 to the intended treatment site, projecting fingers 50 are maintained retracted, pulled back proximally within the lumens 54 to restrain distal portions 56 in a straight configuration and maintain them within the lumens. Upon reaching the intended tissue location, the projecting fingers 50 may be advanced distally so that the distal portions 56 of the fingers are extended through distal ports 58 and become free to return to their natural curved orientation as is shown in FIG. 3A and the end view of the catheter shown in FIG. 3B. Preferably, sufficient distal forces applied to the catheter to cause distal tip 28 to indent a tissue surface 42 so that it herniates around the side surfaces 13 of the catheter providing sufficient tissue depth into which the fingers may project and take hold to restrain the catheter in position during the planned medical procedure. Distal tip 60 of the projecting fingers preferably have a sharpened point suitable for easily penetrating tissue. Longitudinal movement of fingers 50 through the auxiliary lumens 54 is controlled by a control mechanism, which simply comprises a shaft extending from the fingers 50 to the proximal end of the catheter where it may be grasped and manipulated by the physician. The control mechanism need not be a separate component from the finger component but may comprise the proximal portion of a continuous shaft that terminates in the radial finger 50 at its distal end.

Figure 3C:
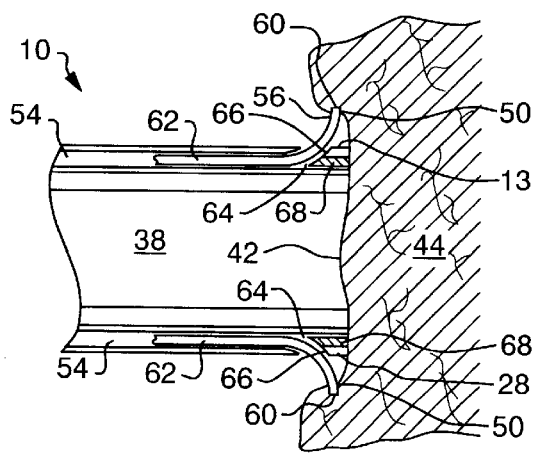
FIG. 3C is a side cut-away view of an embodiment of the catheter positioning system having radially extending fingers containing individual lumens extending from side ports in the catheter.

FIG. 3C shows an alternate embodiment of that shown in FIG. 3A employing side ports 64. The projecting fingers 50 pass through the side ports rather than the distal ports 58, as shown in FIG. 3A. The distal edge of the side port may have a ramp surface 66 to facilitate passage of projecting finger 50 as it is advanced distally and curves resiliently outward through the side port 64. Additionally, ramp-surface inserts 68 may be inserted in the far distal end of the auxiliary lumens 54 to prevent straight distal progress of the projecting fingers 50 when advanced to achieve radial extension.

Figure 4A:
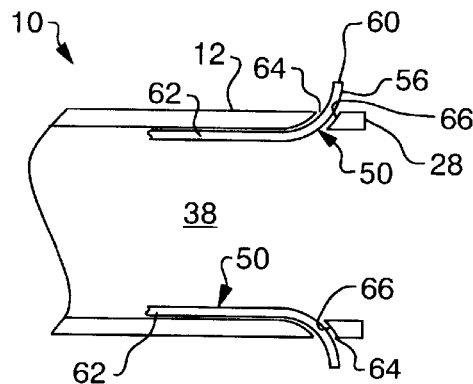
FIG. 4A is a cut-away side view of an embodiment of the catheter positioning system having radially projecting fingers contained in a common catheter lumen and extending through side ports.
Figure 4B:
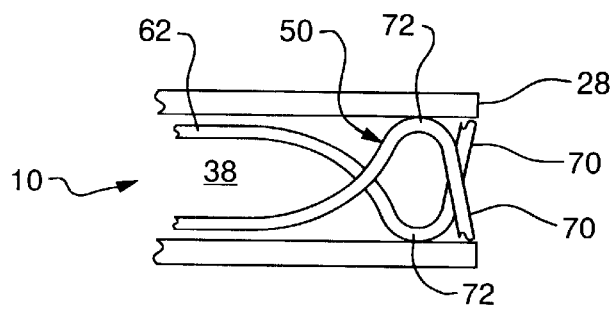
FIG. 4B is a cut-away side view of an embodiment of the catheter positioning system in the retracted position having radially extending fingers contained in a common lumen of the catheter.
Figure 4C:
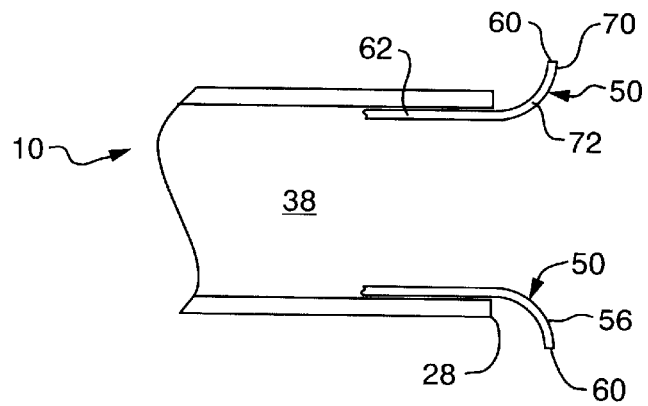
FIG. 4C is a cut-away side view of an embodiment of the catheter positioning system having radially projecting fingers contained in a common catheter lumen and extending through the distal end of the catheter.

FIGS. 4A–4C show an alternative embodiment of the projecting fingers catheter positioning system in which the control mechanism 62 of the fingers passes through the central lumen 38 of the catheter shaft rather than through auxiliary lumens 54 or independent auxiliary lumens 54.

FIG. 4A shows an embodiment having side ports similar to that as shown in FIG. 3C through which the projecting fingers 50 may pass as they extend into surrounding tissue. The distal edge of the side port 64 may have a ramp surface 66 to facilitate the radially extending curvature of the projecting finger 50 at its distal end 56. FIGS. 4B and 4C shown an embodiment of the single lumen catheter 10 in which the projecting fingers exit the lumen at the distal tip 28 of the catheter 28. FIGS. 4B and 4C also show a variation of the projecting finger curvature incorporating a foot-shaped design where each finger has a foot portion 70 that extends substantially perpendicular to the longitudinal axis of the control mechanism 62. Also, the foot configuration comprises a heel portion 72 forming a curved transition between the foot 70 and relatively straight control mechanism portion 62 of the projecting finger 50. The overall effect of the foot configuration is to provide a greater radial extent of the projecting finger 50 into surrounding tissue due to the exaggerated length of foot portion 70.

Figure 5A:
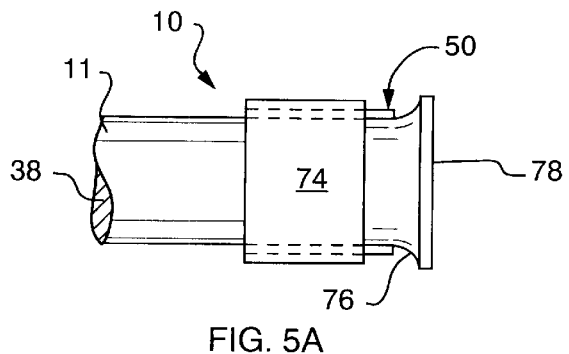
FIG. 5A is a side view of an embodiment of the catheter positioning system having radially extended fingers actuated by an external band, shown in the retracted position.
Figure 5B:
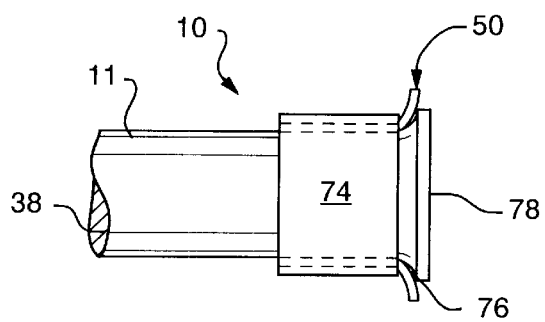
FIG. 5B is the embodiment shown in FIG. 5A in the extended position.

FIGS. 5A–5B show yet another embodiment of the projecting finger catheter positioning system utilizing a band 72, axially slidable along the shaft 11 of the catheter 10 in order to effect extensionary traction of the fingers 50. A slidable band may be formed from any material having relatively low friction properties in comparison to the catheter shaft material. The axial movement of the band may be controlled via a control mechanism such as a cable or shaft extending the length of the catheter through main lumen 38 or an auxiliary lumen or on the exterior of the shaft 11. Alternatively, the band may be considered to represent the distal portion of a full length sheath slid over the catheter shaft 11 and being slidably controllable from the proximal end of the catheter to serve as the control mechanism.

In the embodiment shown in FIGS. 5A and 5B, the filament that forms the projecting fingers 50 is mounted in the band 72 and moves with movement of the band. In this embodiment, the projecting fingers extend distally from the band only a relatively small distance proximally equivalent to the desired maximum radial extent when the fingers are extended. Distal movement of the band and fingers 50 into the ramp surface 76 of outwardly flared flange shaped distal end 78 of the catheter causes the fingers to be pushed radially outward so that they can engage and pierce tissue that will surround the distal tip 78 when a distal force is applied to the catheter. FIG. 5B shows the positioning system in the extended position, with the band 72 being fully advanced distally and fingers extending radially outward after having been driven into the ramp surface 76.

Figure 6A:
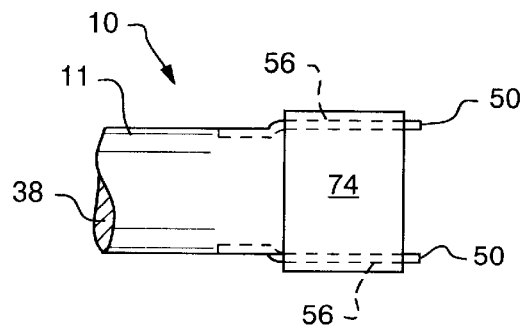
FIG. 6A is an embodiment of the catheter positioning system having radially extended fingers actuated by an external band, shown in the retracted position.
Figure 6B:
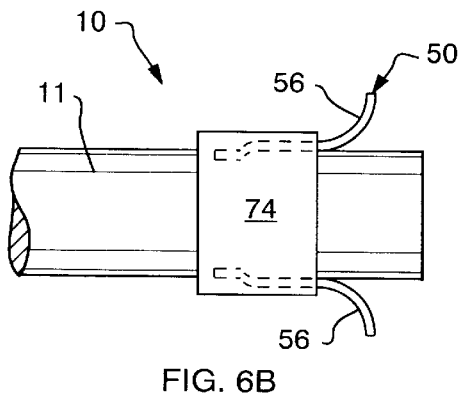
FIG. 6B is a side view of the embodiment shown in FIG. 6A in the extended position.

The embodiment of the radially extending fingers catheter positioning system as shown in FIGS. 6A and 6B also employs a axially slidable band 74 to effect extension and retraction of the fingers; however, the fingers are joined to the catheter shaft 11 rather than to the band 74 as shown in FIGS. 5A and 5B. The effect of this is that the fingers are instead retracted when the band is advanced distally and the fingers are extended when the band is pulled back proximally. Because the fingers are naturally biased to be curved radially outward, the band 74 operates to confine the fingers close to the catheter shaft 11 when extended distally to cover their distal ends 56, as shown in FIG. 6A. As shown in FIG. 6B, proximal withdrawal of the band 74 from the precurved distal area 56 of the fingers permits the fingers to resiliently extend in a radially outward direction from the catheter shaft 11 to penetrate tissue herneating around the distal tip of the catheter. Also, another difference in the embodiment of FIGS. 6A and 6B is that the fingers 50 extend under the force of their inherent resiliency when the band is withdrawn proximally. The fingers 50 in the embodiment shown in FIGS. 5A and 5B are elastically deformed in the extended position because they are driven radially outward as they come into contact with the ramp surfaces 76 of the flanged distal end 78. The forced extension of the fingers in the 5A and 5B embodiments may provide a stronger penetration force if the tissue is needed to secure the catheter in the area of interest.

Figure 7A:
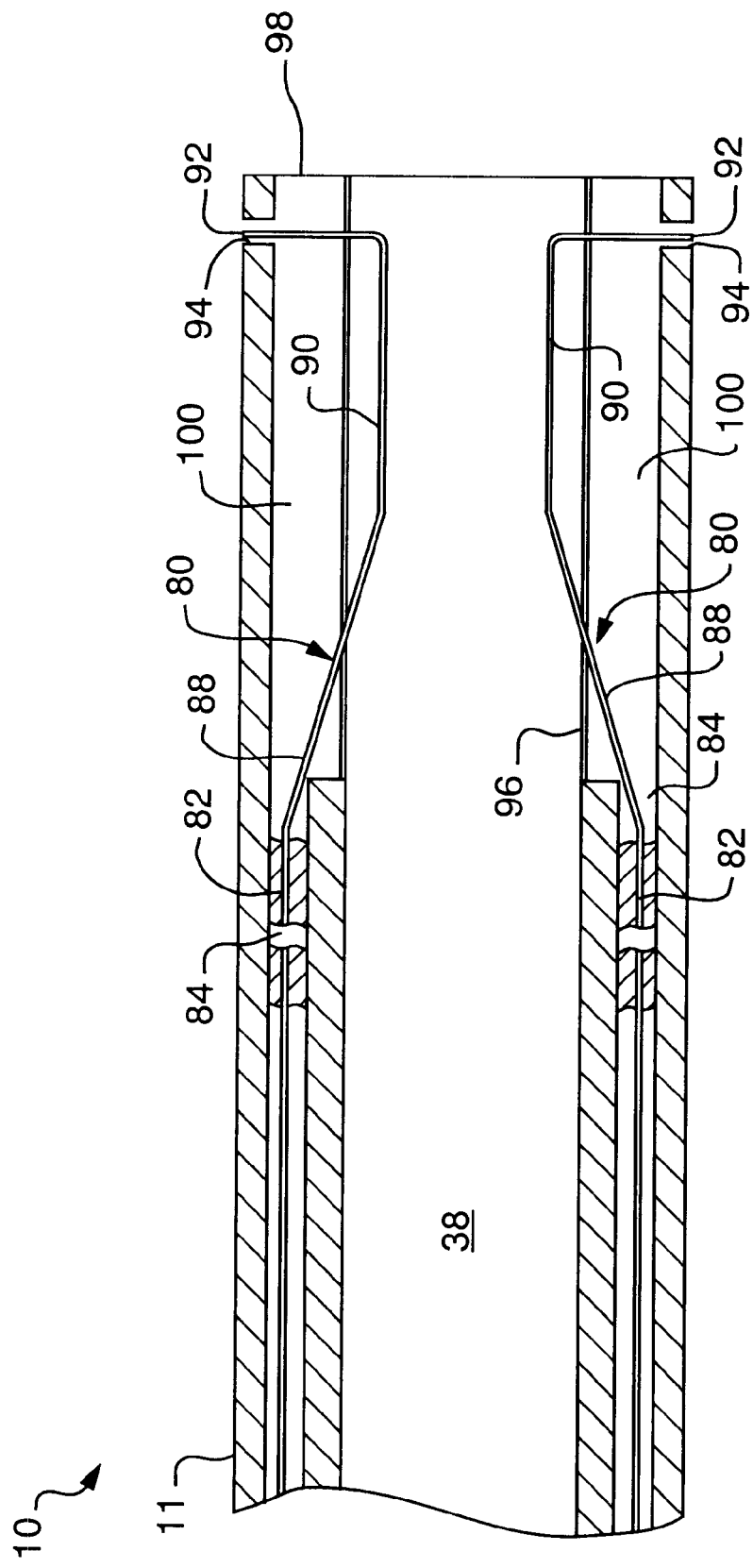
FIG. 7A is a cut-away side view of an embodiment of the catheter positioning system having radially extending fingers actuated by movement of a device through a central lumen of the catheter.
Figure 7B:
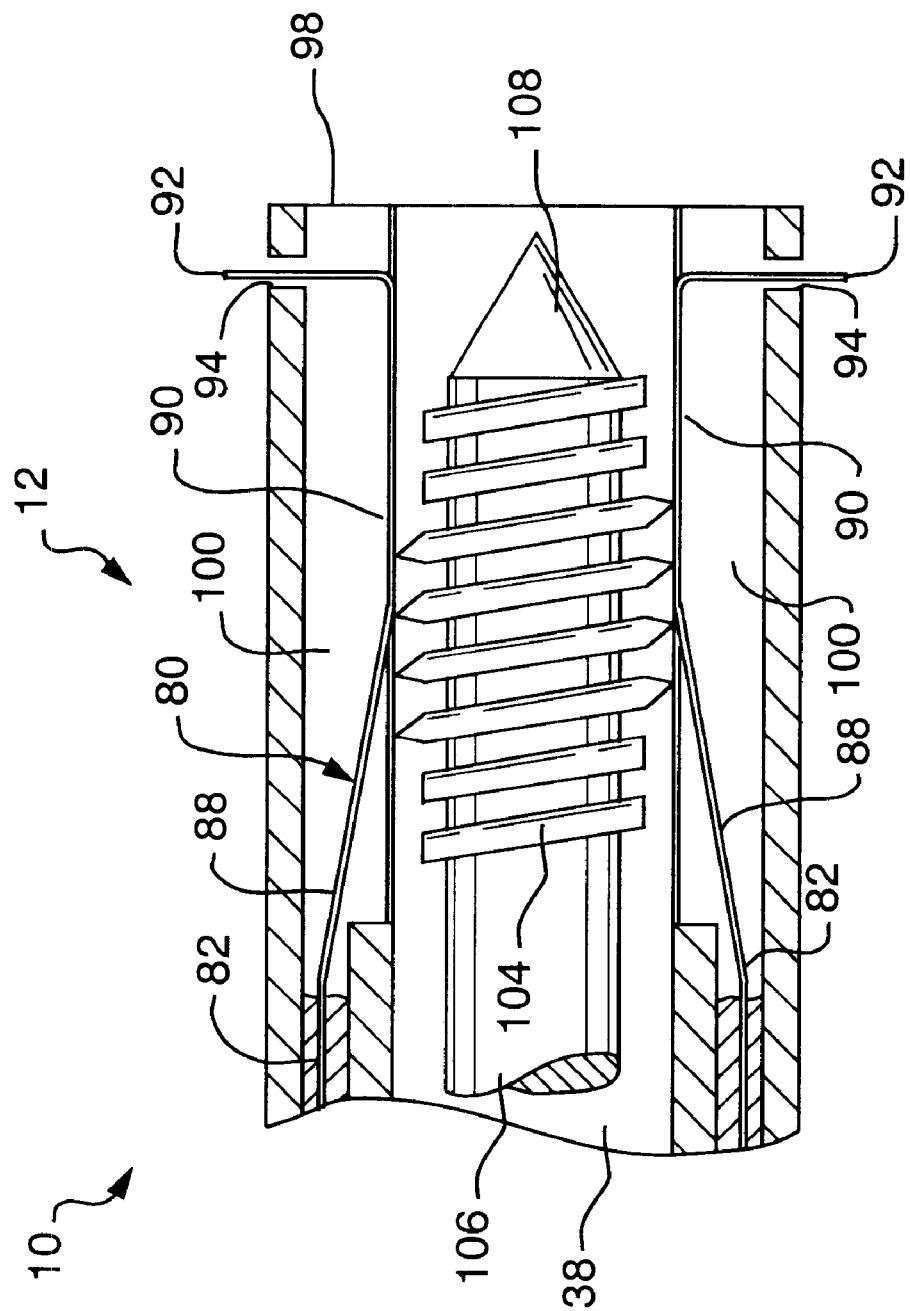
FIG. 7B is a cut-away side view of the embodiment shown in FIG. 7A having a device in the center lumen of the catheter to extend the radially projecting fingers.

FIGS. 7A and 7B show yet another embodiment of the projecting fingers, which utilizes elastic deformation caused by a device being passed through the central lumen 38 of the catheter 10 to extend the fingers. In the absence of a device in the lumen, the fingers resiliently return to their retracted position within the catheter. As shown in FIG. 7A, a cut-away view of the catheter 10 revealing the positioning system, short resilient fingers 80 are mounted inside the catheter shaft, having proximal ends 82 mounted in auxiliary lumens 84 by means such as adhesive 86. Distally from the proximal ends 82 the fingers 80 taper radially inward to form a ramp portion 88, reducing the clearance between the fingers to a distance that is less than the profile of the device to be inserted through the lumen 38 of the catheter. Engagement portions 90 of the fingers 80; therefore, when in contact with the device will cause the distal ends 92 of the fingers, which extend perpendicular to the engagement portions 90, to protrude through side ports 94 as is shown in FIG. 7B. After the device 104 such as an angiogenic implant passes out of the distal end 98 of the catheter and out of engagement with engagement portions 90 of the fingers, the fingers return to their naturally biased retracted position and the catheter distal tip 12 may be pulled away from the tissue.

The device 104 is advanced through the lumen 38 over a shaft 106 having an obturator 108 at its distal end configured to penetrate tissue so that the device 104 can be implanted in the tissue. The shaft 106 extends proximally to the proximal end of the catheter so that it may be manipulated by the physician for delivery of the implant device. The device 104 and shaft 106 are maintained properly square within lumen 38 yet still engage fingers 80 sufficiently to cause them to deform and extend by virtue of slits formed through the inside diameter thickness of the catheter to provide a travel space 100 through which the fingers may have a range of motion as the device passes through. The device is supported around all other areas of the circumference of the lumen 38 except for the areas of the slits. Flexible implant devices may be configured to promote angiogenesis through a variety of mechanisms examples of which are described in detail in pending U.S. patent application Ser. Nos. 09/164,173, 09/211,332 and 09/299,795, which are incorporated by reference herein in their entirety.

In use, the catheter positioning system may be used to deliver an angiogenic implant into myocardial tissue by the steps detailed below. First, the catheter 10 configured as shown in FIGS. 7A and 7B is introduced and navigated to the area of treatment within the left ventricle of the heart, guided by either a guide catheter or a guidewire by conventional techniques. After reaching the general area of treatment, the guidewire, if used, is then removed and the shaft 106 with obturator at 108 and angiogenic device 104 preloaded onto its distal end is then navigated through the lumen of the catheter. The catheter is positioned at the tissue location of interest. A distal force is applied by the physician on both the catheter and the delivery device shaft 106 to not only maintain the distal tip 98 of the catheter against the tissue to be treated, but also to simultaneously advance the device 104 through the lumen 38 and into contact with engagement portions 90 of the fingers 88. This simultaneous motion causes the distal ends 92 of the fingers 88 to penetrate into surrounding tissue to locate the distal tip 98 of the device at a specific location just prior to the devices advancement into the tissue. Depending on the amount of maneuverability needed to reach the intended location with the catheter 10, the stiffness of the material selected for the catheter can be varied to make the catheter more flexible or more rigid.

FIG. 8 shows a variation of the embodiment as shown in FIGS. 7A and 7B, including a handle 110 joined to control mechanisms 112 which are joined to radially extending fingers 88 to provide independent control of the extension or retraction of the fingers rather than an automatic deployment of the fingers illustrated in the last embodiment. Axial movement of the handle 110 causes control mechanism 112 to also move and cause fingers 88 to move in an axial direction. When distal ends 92 of the fingers reach the side ports or exit port at the distal end 98 of the catheter, the fingers will be free to be extended radially outward.

By the foregoing description, it will be appreciated that the invention provides a novel and useful method and device for locating and stabilizing the distal end of a catheter so that a medical procedure can be carried out at a specific treatment site within a patient. The device is easy to use and simple to manufacture.

It should be understood however, that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. A catheter positioning system comprising:

an elongate catheter comprising a tubular shaft having proximal and distal ends and at least one open lumen extending therethrough, and a plurality of resilient members configured to be selectively engaged so that the resilient members extend radially outward from the tubular shaft, each having proximal and distal ends, all distal ends joined together and fixed longitudinally relative to the shaft adjacent its distal end and all proximal ends joined together and to the shaft at a position proximal to the distal end such that the resilient members lie parallel to the longitudinal axis of the shaft when unloaded and such that the resilient members bow radially outward and the distal end of the shaft is rotated through an angular displacement when a compressive load is applied to them;

a control mechanism operatively associated with the resilient members and extending to the proximal end of the shaft and configured to be manipulated by a user to actuate the resilient members from a retracted to an extended position.

2. A catheter positioning system of claim 1 wherein the compressive load is applied by proximal movement of the control mechanism joined to the shaft where the resilient member distal ends are fixed longitudinally to the shaft.

3. A catheter positioning system comprising:

an elongate catheter comprising a tubular shaft having proximal and distal ends, a distal tip and at least one open lumen extending therethrough;

a plurality of resilient members joined to the shaft;

independent control mechanisms operatively associated with each of the resilient members and extending to the proximal end of the shaft and configured to be manipulated by a user to actuate the resilient members from a retracted to an extended position;

each of the resilient members having proximal and distal ends, the proximal ends being in operative association with each control mechanism and their distal ends being free such that movement of the control mechanism in the distal direction causes the distal ends of the members to advance distally through the distal end of the shaft lumen exiting the distal tip and extending radially outward away from the shaft to an extended position, distal to the distal tip.

4. The catheter positioning system of claim 3 wherein movement of the control mechanism in the proximal direction causes the resilient members to move radially inward to a retracted position such that the distal ends of the members do not protrude from the shaft.

5. The catheter positioning system of claim 3 wherein at least one of the resilient members is a tube having a lumen in fluid communication with a therapeutic agent that is pressurized from the proximal end of the shaft.

6. A catheter positioning system comprising:

an elongate catheter comprising a tubular shaft having proximal and distal ends and at least one open lumen extending therethrough;

a plurality of resilient members joined to the shaft;

at least one control mechanism operatively associated with the resilient members and extending to the proximal end of the shaft and configured to be manipulated by a user to actuate the resilient members from a retracted to an extended position;

each of the resilient members having proximal and distal ends, the proximal ends being in operative association with the control mechanism and their distal ends being free such that movement of the control mechanism in the distal direction causes the distal ends of the members to advance radially outward away from the shaft to an extended position;

wherein at least one resilient member has a proximal end joined to a side wall of the shaft and a distal end that is free, the resilient member being naturally biased and arranged relative to the catheter such that the member distal end does not protrude from the catheter until elastically deformed by movement of an object through the lumen of the catheter.

7. The catheter positioning system of claim 6 wherein the object moved through the shaft lumen is an ischemia treatment device.

8. The catheter positioning system of claim 7 wherein the ischemia treatment device comprises a tissue implant and associated delivery device.

9. A catheter positioning system comprising:

an elongate catheter comprising a tubular shaft having proximal and distal ends and at least one open lumen extending therethrough;

a plurality of resilient members joined to the shaft;

at least one control mechanism operatively associated with the resilient members and extending to the proximal end of the shaft and configured to be manipulated by a user to actuate the resilient members from a retracted to an extended position;

each of the resilient members having proximal and distal ends, the proximal ends being in operative association with the control mechanism and their distal ends being free such that movement of the control mechanism in the distal direction causes the distal ends of the members to advance radially outward away from the shaft to an extended position;

wherein the proximal ends of the resilient members are fixed to the catheter shaft and are arranged to be contacted by the control mechanism advancing distally through the lumen of the shaft to push the distal ends of the resilient member radially outward.

10. The catheter positioning system of claim 9 wherein the proximal ends of the members extend at least partially into the lumen of the shaft and the shaft further comprises sideports through which the distal ends of the members may pass to extend radially outward.

11. The catheter positioning system of claim 9 wherein the control mechanism comprises an implant delivery system.

12. A catheter positioning system comprising:

an elongate catheter comprising a tubular shaft having proximal and distal ends, a distal tip, at least one open lumen extending therethrough, and a plurality of auxiliary lumens terminating at distal ports at the distal tip of the shaft;

a plurality of resilient members, each slidably arranged through an auxiliary lumen;

at least one control mechanism operatively associated with the resilient members and extending to the proximal end of the shaft and configured to be manipulated by a user to actuate the resilient members from a retracted to an extended position;

each of the resilient members having proximal and distal ends, the proximal ends being in operative association with the control mechanism and their distal ends being free such that movement of the control mechanism in the distal direction causes the distal ends of the members to advance distally through the distal ports at the distal tip of the shaft and radially outward away from the shaft to an extended position.

13. A catheter positioning system comprising:

an elongate catheter comprising a tubular shaft having proximal and distal ends and at least one open lumen extending therethrough;

a plurality of resilient members joined to the shaft;

at least one control mechanism operatively associated with the resilient members and extending to the proximal end of the shaft and configured to be manipulated by a user to actuate the resilient members from a retracted to an extended position;

each of the resilient members having proximal and distal ends, the proximal ends being in operative association with the control mechanism and their distal ends being free such that movement of the control mechanism in the distal direction causes the distal ends of the members to advance radially outward away from the shaft to an extended position;

wherein the control mechanism comprises a sleeve longitudinally slidable over the shaft to control the extension of the resilient members.

14. The catheter positioning system of claim 13 wherein the proximal end of the resilient members is mounted in a sidewall of the shaft and the sleeve engages the member to control its extension.

15. The catheter positioning system of claim 14 wherein the resilient members are biased radially outward and sliding movement of the sleeve serves to engage and confine the resilient members against the catheter shaft.

16. The catheter positioning system of claim 13 wherein the proximal end of the resilient member is mounted to the sleeve and longitudinal movement of the member along the shaft into contact with a ramped surface controls radial extension of the member.

17. An elongate catheter comprising:

a tubular shaft having proximal and distal ends, at least one open central lumen extending through the shaft and at least one side port through the shaft to the lumen adjacent the distal end of the shaft, the port having a distal wall that is sloped to form a ramp surface;

a plurality of resilient members extending through the central lumen;

at least one control mechanism operatively associated with the resilient members and extending from the lumen to the proximal end of the shaft and configured to be manipulated by a user to actuate the resilient members from a retracted to an extended position;

each of the resilient members having proximal and distal ends, the proximal ends being in operative association with the control mechanism and their distal ends being free such that movement of the control mechanism in the distal direction causes the distal ends of the members to advance distally and be guided by the ramp surface radially outward through the side ports and away from the shaft to an extended position.

* * * * *